United States Patent

Tuneberg

[11] Patent Number: 5,320,526
[45] Date of Patent: Jun. 14, 1994

[54] BUCCAL TUBE INSERT
[75] Inventor: Lee Tuneberg, Sheboygan, Wis.
[73] Assignee: American Orthodontics, Sheboygan, Wis.
[21] Appl. No.: 988,737
[22] Filed: Dec. 10, 1992
[51] Int. Cl.$^5$ ............................................. A61C 3/00
[52] U.S. Cl. ............................................. 433/17; 433/16
[58] Field of Search ........................... 433/17, 16, 13, 18

[56] References Cited

U.S. PATENT DOCUMENTS

| | | | |
|---|---|---|---|
| 4,496,318 | 1/1985 | Connelly, Jr. | 433/14 |
| 4,498,867 | 2/1985 | Kesling | 433/16 |
| 4,781,582 | 11/1988 | Kesling | 433/17 |
| 4,927,362 | 5/1990 | Snead | 433/17 |
| 4,963,092 | 10/1990 | Snead | 433/17 |
| 5,151,028 | 9/1992 | Snead | 433/17 |

Primary Examiner—Gene Mancene
Assistant Examiner—Cindy A. Cherichetti
Attorney, Agent, or Firm—Godfrey & Kahn

[57] ABSTRACT

A buccal tube insert including a frusto-conically shaped main body having a predetermined cross-sectional dimension and which defines a longitudinally disposed passageway which extends substantially therethrough, the main body disposed in friction fitting relation within a lumen defined by a buccal tube.

18 Claims, 4 Drawing Sheets

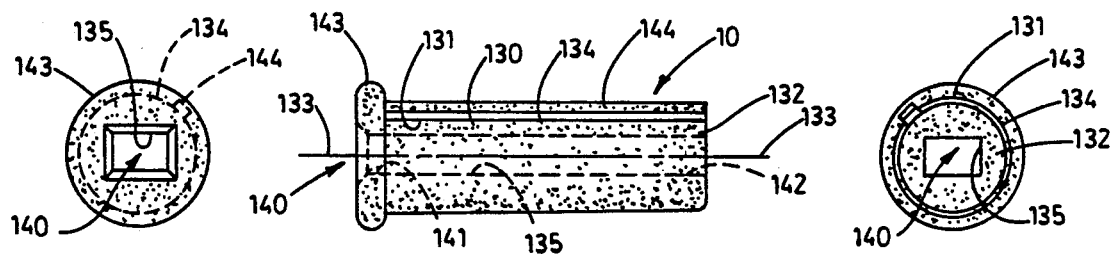
FIG. 8A  FIG. 8B  FIG. 8C
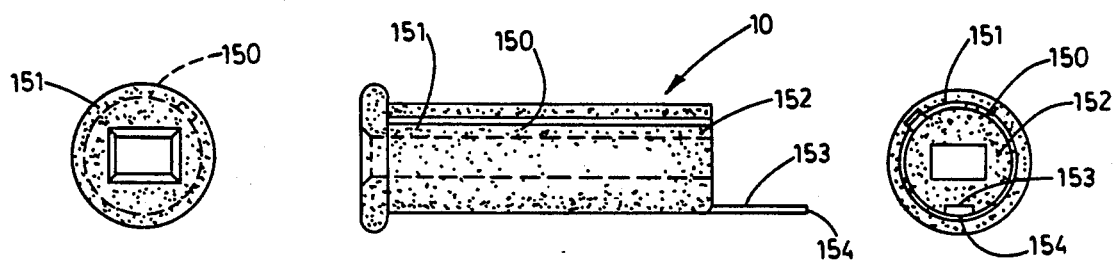
FIG. 9A  FIG. 9B  FIG. 9C
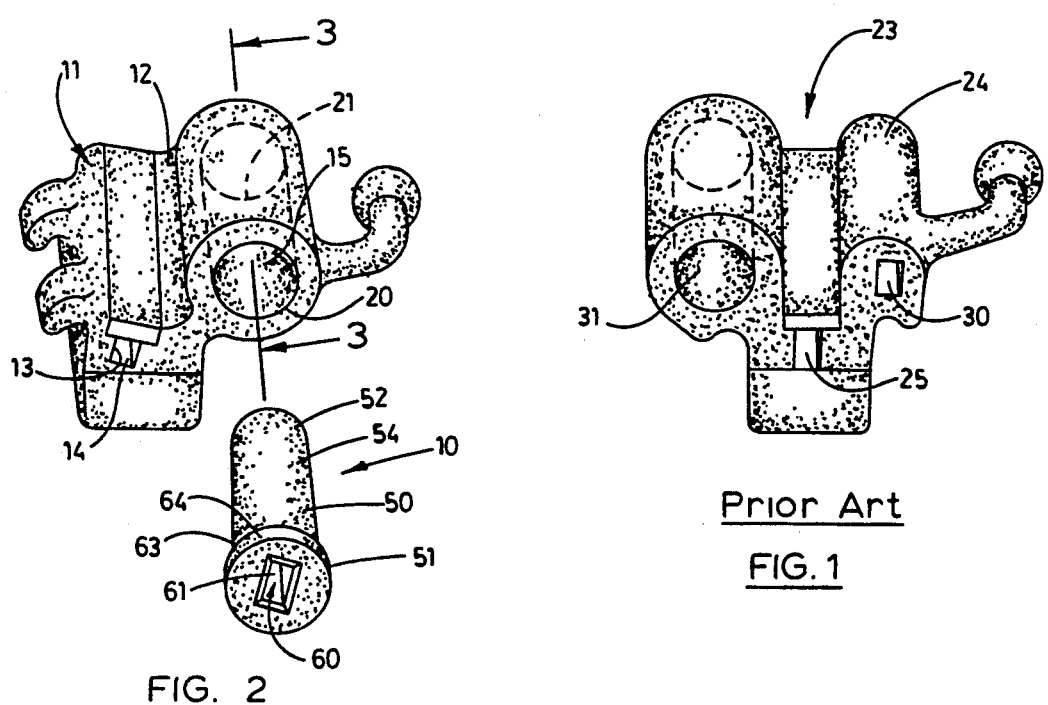
FIG. 2
Prior Art
FIG. 1

BUCCAL TUBE INSERT

BACKGROUND OF THE INVENTION

1. Field of the Invention

The present invention relates in general to an orthodontic appliance which is mounted on a tooth during the treatment of a malocclusion, and more particularly, to such an appliance which converts a round buccal tube into a buccal tube which has a substantially square or rectangular cross-section.

2. Description of the Prior Art

The prior art is replete with numerous examples of assorted orthodontic appliances which may be temporarily mounted on or affixed to the exterior surface of a tooth and which are operable to receive various arch wires which are used thereafter to correct the individual patients' malocclusions. In view of the many biomechanical considerations which affect the treatment of a selected malocclusion, manufacturers of orthodontic supplies often provide many types of buccal tubes with a majority, being classified generally as "single", "double", and "triple" tubes. As should be understood, these tubes may be stamped, machined, cast, or manufactured from sintered powered metal.

As a general matter, single buccal tubes are considered comfortable and hygienic for the patient, however, they have shortcomings inasmuch as they offer only a single, rectangular, arch wire slot for receiving the arch wire during orthodontic treatment. Further, a "double" tube normally offers a rectangular arch wire slot and a round tube for auxiliary use such as for a facebow. The "double tube" normally allows for treatment options designated at predetermined intervals by the orthodontist. Alternatively, other forms of double tubes are available and may offer two rectangular arch wire slots thereby eliminating the round tube. In this regard, the additional rectangular tube allows for the use of sectional arch wires or what have been termed "intrusion arch wires", that is, those arch wires that are connected at the molars and which by-pass the bicuspids and cuspids and only engage the four anterior teeth.

As noted above, and in view of the multitude of treatment considerations, many clinicians will employ a "triple tube". These triple tubes are often manufactured with two rectangular arch wire slots, and a round tube.

While the triple tube provides a convenient means for increasing the treatment options available to a clinician, and therefore, has many laudable benefits, there are many shortcomings which detract from its usefulness. For example, all three lumens, or passageways defined by the triple tube, are rarely simultaneously used during treatment. Additionally, and due to design considerations, the triple buccal tube must be, large, relatively speaking, in the occluso-gingival dimension to accommodate or define the three-lumens. Another shortcoming attendant to the use of triple buccal tubes is that they can present clinical problems vis-a-vis placement on the tooth, potential hygiene problems, and patient discomfort.

Therefore, it has long been known that it would be desirable to have an orthodontic appliance which may be utilized to treat malocclusions and which has the treatment flexibility provided by a triple buccal tube, but, alternatively, has a size, compactness and convenience normally attendant with the use of a double buccal tube.

SUMMARY OF THE INVENTION

Therefore, it is an object of the present invention to provide a buccal tube insert.

Another object of the present invention is to provide a buccal tube insert which may be received in telescoping, friction-fitting relation in the facebow lumen of a double buccal tube, the buccal tube insert further defining a rectangular or square shaped passageway that traverses the length of the insert in the mesial-distal direction.

Another object of the present invention is to provide a buccal tube insert which has a main body that is generally frusto-conically shaped, and wherein the main body has opposite first and second ends, and wherein the first end has a diametral dimension greater than the facebow lumen of the double buccal tube.

Another object of the present invention is to provide a buccal tube insert, and wherein a radially extending member is made integral with the exterior facing surface of the buccal tube insert and is located at the first end of the main body.

Another object of the present invention is to provide a buccal tube insert which includes a deformable member which is made integral with the second end of the main body, and which extends longitudinally outwardly relative thereto, the deformable member deformed in a direction substantially radially outwardly following placement of the buccal tube insert in the facebow lumen thereby impeding removal of the buccal tube insert.

Another object of the present invention is to provide a buccal tube insert, and wherein the facebow lumen includes a longitudinally disposed groove, and wherein a tongue is made integral with the main body of the buccal tube insert and is operable to be slideably received in interlocking relation relative to the groove thereby impeding rotation of the buccal tube insert.

Another object of the present invention is to provide a buccal tube insert, and wherein the passageway defined by the main body of the buccal tube insert has a substantially uniform dimension throughout its length, and which is operable to receive a rectangular, or square shaped arch wire for sectionals, or intrusion arches.

Another object of the present invention is to provide a buccal tube insert which is characterized by ease of installation, simplicity of construction, and which can be manufactured and sold at a nominal price.

Further objects and advantages of the present invention are to provide a buccal tube insert for use in converting a double buccal tube to an alternative form which provides greater flexibility vis-a-vis treatment options for the clinician; the buccal tube insert received within the face bow lumen of the double buccal tube.

BRIEF DESCRIPTION OF THE DRAWINGS

FIG. 1 is a perspective view of a triple buccal tube.

FIG. 2 is a somewhat enlarged perspective view of a double buccal tube, and which is operable to receive the buccal tube insert of the present invention.

FIG. 8A is an end view of the fifth form of the invention.

FIG. 8B is a side elevation view of the fifth form of the invention.

FIG. 8C is an end view of the fifth form of the invention taken from a position opposite to that shown in FIG. 8A.

FIG. 9A is an end view of the sixth form of the invention.

FIG. 9B is a side elevation view of the sixth form of the invention.

FIG. 9C is an end view of the sixth form of the invention taken from a position opposite to that shown in FIG. 9A.

DESCRIPTION OF THE PREFERRED EMBODIMENT

FIRST FORM

Figure 10:
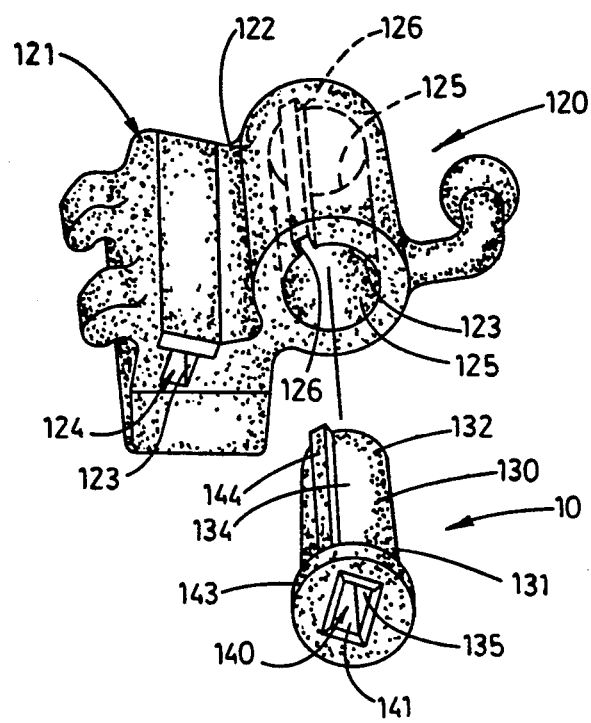
FIG. 10 is a somewhat enlarged perspective view of a double buccal tube and which is operable to receive one form of the buccal tube insert of the present invention.

Referring more particularly to the drawings, the first form of the buccal tube insert of the present invention is generally indicated by the numeral 10 in FIG. 2. As should be understood, all forms of the buccal tube insert find utility when employed in combination with a prior art double buccal tube which is best illustrated by the numeral 11 in FIG. 2. As shown therein, the prior art double buccal tube includes a main body 12 which defines a square or rectangular shaped lumen or passageway 13. Additionally, the main body 12 has an inside facing surface 14 which defines a round or cylindrically lumen 15. The cylindrically shaped lumen normally accommodates a facebow, not shown. Further, the round or cylindrically shaped lumen 15 has a mesial or first end 20, and an opposite, second or distal end 21.

As noted earlier, the prior art practice includes the use of a triple buccal tube such as that shown at numeral 23 in FIG. 1. As shown therein, the prior art triple buccal tube includes a main body 24 which defines a rectangular lumen 25; a rectangular-shaped lumen 30; and a round or cylindrically shaped lumen 31. As discussed earlier, the prior art triple buccal tubes, while producing many laudable results, have several shortcomings which have detracted from their usefulness.

Figures 4A, 4B, 4C:
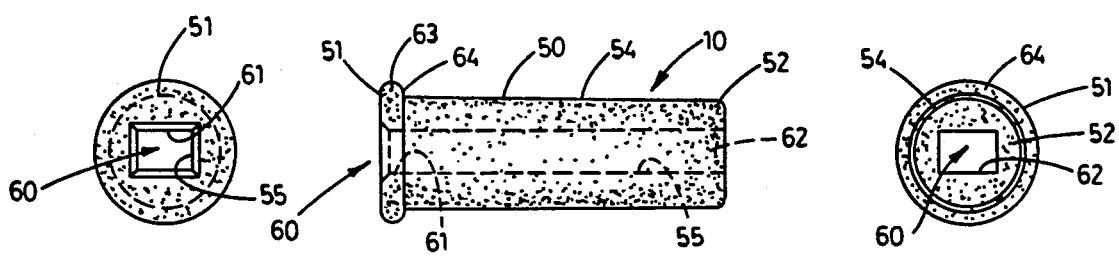
FIG. 4A is a somewhat enlarged end view of the first form of the invention.
FIG. 4B is a somewhat enlarged side elevation view of the first form of the invention.
FIG. 4C is an end view of the first form of the invention taken from a position opposite to that shown in FIG. 4A.

The first form of the present invention is best illustrated by reference to FIGS. 4A, 4B, and 4C, respectively. As shown therein, the buccal tube insert 10 has a main body 50 which has a first or mesial end 51, and an opposite, second, or distal end 52. Further, the main body, which is substantially frusto-conically shaped, is defined by a longitudinal axis that is identified by the line which is labeled 53. Additionally, the main body has an exterior facing surface 54, and an opposite interior facing surface 55. The interior facing surface defines a substantially rectangular shaped passageway 60. The passageway is substantially uniform along its entire length, although, conceivably, it is possible that the passageway could be discontinuous, or alternatively, could have a variable cross-sectional dimension. The main body of the buccal tube insert 10 is manufactured by metal injection molding. There are, of course, other manufacturing techniques which could be employed to produce a similarly shaped object. Further, and while the exterior surface is illustrated as being textured, the surface may be completely smooth, or alternatively, a discrete portion may be textured to provide a better friction-fit when employed. This will be discussed in greater detail hereinafter. Additionally, it will be noted, that while the exterior facing surfaces of the buccal tube are shown as having a texture, they similarly may have a completely smooth finish.

Figure 3:
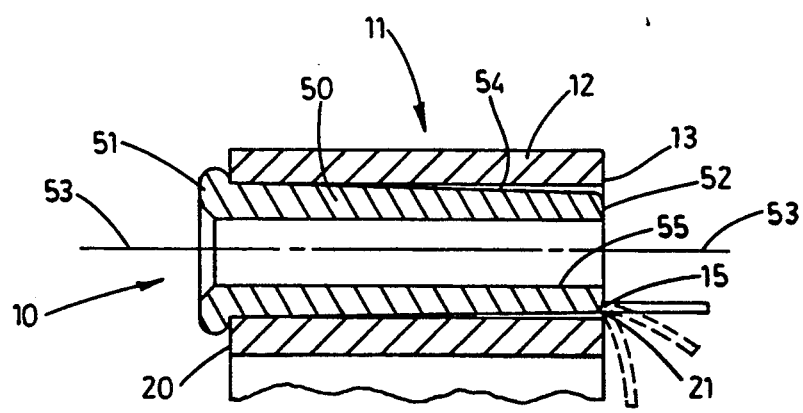
FIG. 3 is a somewhat enlarged longitudinal sectional view of the first form of the invention taken from a position along line 3—3 of FIG. 2.

As best illustrated by reference to FIGS. 4A and 4B, the first form of the invention includes a substantially circumscribing collar 63 which is mounted on or made integral with the first or mesial end 61 of the main body 50. The circumscribing collar has an exterior facing surfacing 64 which is located substantially radially outwardly relative to the exterior facing surface 54. The circumscribing collar acts as a stop member when the buccal tube insert is slideably received in the cylindrical lumen 15. This is best seen by reference to FIG. 3.

As noted above, the main body 50 of the buccal tube 10 has a substantially frusto-conical shape. In this regard, it should be understood that the outside diametral dimension of the main body 50, when measured at the first end 51, is somewhat greater than the diametral dimension of the lumen 15 which is defined by the main body 12, of the double buccal tube 11. As will be appreciated, the interior facing surface 55 of the main body 50 defines a substantially rectangular shaped passageway 60 that traverses the length of the main body 15 from the first end 51 to the second end 52. This rectangular passageway of course, can accommodate sectional, or intrusion arches, not shown, when required by the clinician. Thus, the orthodontist may use the rectangular arch slot 13 for the majority of treatment, and further may use the round or cylindrically shaped passageway 15 for a facebow. Additionally, the clinician may convert the round passageway 15 into a square passageway, when conditions warrant, by placing the buccal tube insert 10 into telescoping, friction-fitting relation relative to the round or cylindrically shaped lumen 15, thereby converting it into a rectangular arch wire slot for sectional or intrusion arches. In this fashion, a clinician avoids the need for utilizing the prior art triple buccal tube 23 which has the attendant shortcomings discussed, earlier.

SECOND FORM

Figures 5A, 5B, 5C:
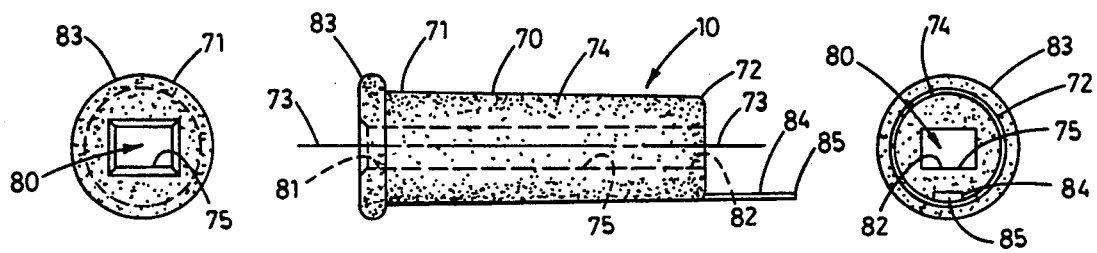
FIG. 5A is an end view of the second form of the invention.
FIG. 5B is a side elevation view of the second form of the invention.
FIG. 5C is an end view of the second form of the invention taken from a position opposite to that shown in FIG. 5A.

The second form of the present invention has many features similar to the first form of the invention. For example, the second form of the invention includes a substantially frusto-conically shaped main body 70, having a first or mesial end 71, and an opposite, second, or distal end 72. The second form similarly has a longitudinal axis defined by the line labeled 73, and has an exterior facing surface 74, and an opposite, interior facing surface 75. Additionally, the outside diameter of the main body, when measured at the first or mesial end, is greater than the diametral dimension of the round or cylindrically shaped lumen 15, which is defined by the double buccal tube 11. The interior facing surface 75 defines a passageway 80 which may be either square or rectangular shaped, and which extends from the first to the second ends, thereof, although, conceivably, this passageway could be discontinuous or alternatively, have a variable inside cross-sectional dimension. The passageway has a first, or mesial end 81, and an opposite, second, or distal end 82. Similarly, the second form of the invention has a substantially circumscribing collar 83 which is mounted on, or otherwise made integral with, the first end 71. The second form of the invention further includes a deformable member 84 which is made integral with the second or distal end 72, and which extends substantially longitudinally outwardly relatively thereto. As best seen in FIG. 5B, the deformable member has an extreme distal end 85 which, when the buccal tube insert 10 is appropriately placed in frictional receiving engagement relative to the round or cylindrically shaped lumen 15 of the prior art double buccal tube 11, is subsequently deformed or otherwise urged or bent radially outwardly relative to the longitudinal axis 73 thereby impeding removal of the buccal tube insert from the lumen 15 of the double buccal tube 11. This is best seen by a study of FIG. 3.

In all other respects, the second form of the invention operates in the same fashion as the first form of the invention.

THIRD FORM

Figures 6A, 6B, 6C:
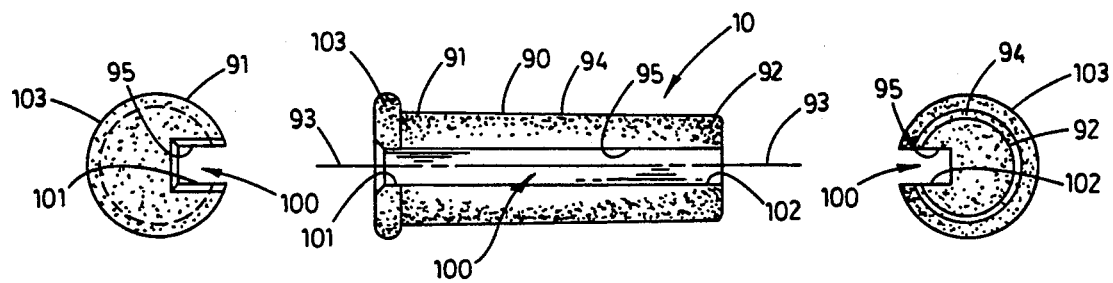
FIG. 6A is an end view of the third form of the invention.
FIG. 6B is a side elevation view of the third form of the invention.
FIG. 6C is an end view of the third form of the invention taken from a position opposite to that shown in FIG. 6A.

The third form of the invention 10 is best illustrated by reference to FIGS. 6A, 6B, and 6C, respectively. As shown therein, the third form of the invention has a main body 90, which includes a first or mesial end 91, and an opposite, second, or distal end 92. The third form of the invention also includes a longitudinal axis which is generally indicated by the line labeled 93. The main body further has an exterior facing surface 94, and an interior facing 95. As best illustrated in FIG. 6A, the interior facing surface 95 defines a substantially rectangular or square shaped slot or passageway 100 which extends from the first to the second ends 101 and 102, respectively, although conceivably, it is possible that this same slot may be discontinuous, or alternatively, have varying cross-sectional dimensions. When the main body is appropriately placed or disposed in telescoping, frictional receiving relationship relative to the cylindrically shaped lumen 15, of the prior art double buccal tube 11, the slot then becomes, a substantially rectangular or square shaped passageway which can accommodate arch wires having that particular cross-sectional shape. As best shown in FIG. 6B, a discontinuous collar 103 is mounted on, or made integral with the first or mesial end 91, of the main body 90. As should be understood, the third form of the invention has the same diametral characteristics as discussed earlier with respect to the first and second forms of the invention, and therefore these facets of the invention, for purposes of brevity, are not discussed in further detail herein. Similarly, the third form of the invention has a substantially frusto-conically shaped body 90, which, when received in the lumen 15 frictionally engages the inside facing surface 14 of the prior art double buccal tube 11 thereby securing the buccal tube insert 10 in an appropriate attitude or position to receive arch wires for use in correcting various malocclusions.

FOURTH FORM

Figures 7A, 7B, 7C:
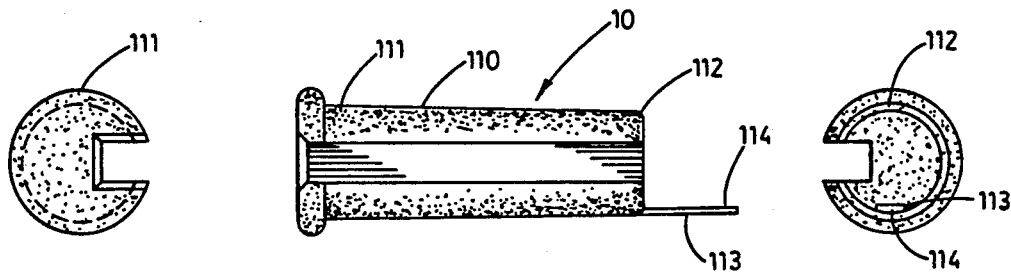
FIG. 7A is an end view of the fourth form of the invention.
FIG. 7B is a side elevation view of the fourth form of the invention.
FIG. 7C is an end view of the fourth form of the invention taken from a position opposite to that shown in FIG. 7A.

The fourth form of the present invention 10 is generally shown in FIGS. 7A, 7B, and 7C, respectively. As illustrated therein, the fourth form of the invention includes many of the features of the third form of the invention, that is, it has a main body 110 which includes a first or mesial end 111, and an opposite, second, or distal end 112. In all other respects, it is substantially identical. The fourth form of the invention additionally includes a deformable member 113 which is mounted on, or made integral with the second or distal end 112, and which extends substantially longitudinally outwardly relative thereto. The deformable member 113 has an extreme distal end 114. In all other respects, the deformable member operates in a fashion similar to that described earlier with respect to the second form of the invention and therefore, for purposes of brevity, is not discussed further detail herein.

FIFTH FORM

The fifth form of the invention is generally shown in FIG. 10. As illustrated therein, a modified, double buccal tube 120 has a main body 121, which has an exterior facing surface 122, and an opposite interior facing surface 123. The interior facing surface defines a square or rectangular shaped lumen 124, and a generally round or cylindrically shaped lumen 125. As shown in FIG. 10, a longitudinally disposed groove or channel 126 is formed in the interior facing surface 123 and extends from the mesial end of to the distal end thereof.

The fifth form of the invention 10 includes a main body 130, which is substantially frusto-conically shaped, and which further has the same diametral dimensions which were earlier discussed with respect to the other forms of the invention. The main body 130 of the fifth form of the invention has a first or mesial end 131, and a second, opposite, or distal end 132. Further, the main body is defined by a longitudinal axis which is indicated by the line labeled 133. The main body further has an exterior facing surface 134, and an opposite, interior facing surface 135. The interior facing surface 135 defines a rectangular or square shaped passageway 140 which extends from the first end to the second end, but which may, under appropriate circumstances, be discontinuous. The cross-sectional dimensions of the rectangular or square shaped passageway 140 are substantially constant along its entire length although it is possible that a passageway having a variable cross-sectional dimension may be employed. The passageway has a first or mesial end 141, and an opposite second or distal end 142. The fifth form of the invention also includes a circumscribing collar 143 having the characteristics as earlier described with respect to the earlier forms of the invention.

As best shown in FIGS. 8A and 10, an elongated tongue 144 is made integral with the exterior facing surface 134 and extends in a substantially longitudinal direction along the exterior facing surface from the first end 131, toward the second end 132. Alternatively, it is possible that the tongue may include a small, discontinuous member (not shown) rather than a continuous elongated tongue as shown in the drawings. However, the operation of the fifth form of the invention will be substantially identical. As should be appreciated, the tongue 144 has a width or transverse dimension, as well as a height or radially disposed dimension, which permits it to be slideably received in interfitting substantially locking relation relative to the groove or channel 126. This is very similar to a key and keyway combination. When the buccal tube insert 10 is received within the lumen 125, the tongue and corresponding groove or channel positions the buccal tube insert in an appropriate attitude to receive the arch wires which were described earlier. It should be readily apparent that the present arrangement impedes rotation of the buccal tube insert about the longitudinal axis 133.

SIXTH FORM

The sixth form of the invention is illustrated in FIGS. 9A, 9B, and 9C. The sixth form of the invention includes a main body 150, which has a first or mesial end 151, and an opposite, distal, or second end 152. The sixth form of the invention is otherwise identical to the fifth form of the invention but further includes a deformable member 153 which is made integral with the second, or distal end 152, and which extends substantially longitudinally outwardly relative thereto. The deformable member has an extreme distal end 154 which operates in a fashion similar to the second form of the invention and therefore, for purposes of brevity, is not discussed in further detail herein.

SEVENTH FORM

Figure 11A:
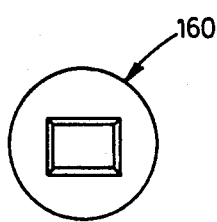
FIG. 11A is an end view of the seventh form of the invention.
Figure 11B:
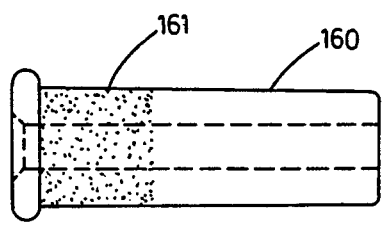
FIG. 11B is a side elevation view of the seventh form of the invention.
Figure 11C:
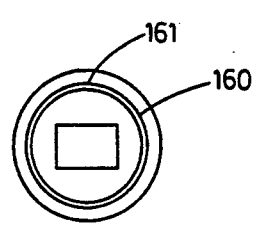
FIG. 11C is an end view of the seventh form of the invention taken from a position opposite to that shown in FIG. 11A.

The seventh form of the invention is best seen by reference to FIGS. 11A, B, and C, respectively. As earlier discussed, the seventh form of the invention has substantially the identical characteristics of the first form of the invention with the exception of the exterior surface 160 which has a discrete textured area 161 formed thereon. As will be appreciated, all other surfaces are substantially smooth. In the present form of the invention, the textured surface is provided to enhance the friction fit of the device with an accompanying buccal tube. This same concept can be applied to the earlier described forms of the invention.

OPERATION

The operation of the described embodiments of the present invention are believed to be readily apparent and are briefly summarized at this point.

As a general matter, all six forms of the present invention operate generally in the same fashion, that is, they each include a mesial end which has a diametral dimension greater than the lumen in which they are received, thereby providing a friction-fit. In several forms of the invention, that is, the second, fourth and sixth forms of the invention, the invention also includes a deformable member which, when deformed substantially radially, outwardly, impedes the removal of the buccal tube insert 10 from the double buccal tube 11. Alternatively, and in the sixth form of the invention, a tongue 144 is provided which fits in slidable mating relation within a keyway or groove 126. In this fashion, the buccal tube insert of the sixth form of the invention is impeded from rotating about the longitudinal axis 133.

It will be seen, therefore, that the present invention provides a convenient, expedient, and inexpensive means by which a clinician may easily convert a double buccal tube 11 into an alternative appliance which may accommodate square or rectangular shaped arch wires, and further provides a fully dependable and practical means by which the double buccal tubes may be converted, without resort to replacing the entire buccal tube when the clinical situation warrants.

Although the invention has been herein shown and described in what is conceived to be the most practical and preferred embodiments it will be recognized that departures may be made therefrom within the scope of the invention which is not to be limited to the illustrative details disclosed.

What I claim:

1. A buccal tube insert which is operable to coact with a double buccal tube, the double buccal tube having a main body which includes a mesoidistally extending and substantially cylindrically shaped lumen, and a rectangularly shaped lumen, and wherein the respective lumens are defined by a continuous wall, the buccal tube insert comprising:

a main body having a predetermined cross-sectional dimension, and exterior surface, and opposite first and second ends, and wherein the main body defines a passageway which extends from the first end in the direction of the second end, and wherein the main body of the buccal tube insert is frusto-concially shaped, and wherein the diametral dimension of the first end is greater than the diametral dimension of the second end, and the diametral dimension of the first end is greater than the diametral dimension of the lumen, and wherein the main body is operable to be received within the cylindrically shaped lumen which is defined by the double buccal type.

2. A buccal tube insert as claimed in claim 1, and wherein a stop member for impeding movement is made integral with the exterior surface and is located at the first end of the main body, the stop member extending substantially radially outwardly relative to the exterior surface.

3. A buccal tube insert as claimed in claim 2, and wherein the stop member includes a circumscribing collar, and wherein the passageway defined by the main body has a square or rectangular shape.

4. A buccal tube insert as claimed in claim 3, and wherein a deformable member is made integral with the second end of the main body and extends longitudinally outwardly relative thereto, the deformable member deformed in a direction substantially radially outwardly following placement of the buccal tube insert in the lumen of the buccal tube thereby impeding removal of the buccal tube inset.

5. A buccal tube insert as claimed in claim 2, and wherein the passageway defined by the buccal tube insert is a longitudinally disposed slot which is formed in the main body and which extends from the first end to the second end.

6. A buccal tube insert as claimed in claim 5, and wherein a deformable member is made integral with the second end of the main body and extends substantially longitudinally outwardly thereto, the deformable member deformed substantially radially outwardly following placement of the buccal tube insert in the lumen of the buccal tube thereby impeding removal of the buccal tube insert.

7. A buccal tube insert as claimed in claim 2, and wherein the substantially cylindrically shaped lumen of the double buccal tube includes a longitudinally disposed groove, and wherein a tongue is made integral with the main body of the buccal tube insert and is operable to be slidably received in interlocking relation relative to the groove thereby impeding rotation of the buccal tube insert.

8. A buccal tube insert as claimed in claim 7 and wherein a deformable member is made integral with the second end of the main body and extends substantially longitudinally, outwardly relative thereto, and wherein the deformable member is deformed substantially longitudinally outwardly following placement of the buccal tube insert in the lumen of the buccal tube thereby impeding removal of the buccal tube.

9. A buccal tube insert which is received within a substantially cylindrically shaped lumen which is defined by a double buccal tube, and wherein the cylindrically shaped lumen is defined by a continuous wall, the buccal tube insert comprising:
a substantially frusto-conically shaped main body having an exterior facing surface which frictionally engages the continuous wall of the double buccal tube thereby releasably positioning the buccal tube insert in substantially fixed relation relative to the double buccal tube, and first and second ends, and wherein the main body further includes a circumscribing collar which is made integral with the exterior surface and which extends substantially radially outwardly therefrom, and wherein a longitudinally disposed passageway is defined by the main body of the buccal tube insert, and which extends from the first end to the second end.

10. A buccal tube insert as claimed in claim 9, and wherein the first end of the main body has a diametral dimension greater than the diametral dimension of the cylindrically shaped lumen, and the diametral dimension of the second end is less than the first end, and wherein the circumscribing collar is positioned on the first end of the main body.

11. A buccal tube insert as claimed in claim 10, and wherein a deformable member is made integral with the second end of the main body and extends substantially longitudinally outwardly relative thereto, the deformable member being deformed substantially radially outwardly following placement of the buccal tube insert in the cylindrically shaped lumen of the buccal tube thereby impeding removal of the buccal tube insert.

12. A buccal tube insert as claimed in claim 11, and wherein the passageway defined by buccal tube insert has a square or rectangular cross-section which is substantially uniform along its entire length.

13. A buccal tube insert as claimed in claim 11, and wherein the passageway defined by the buccal tube insert is a substantially longitudinally disposed slot which extends from the first end to the second end.

14. A buccal tube insert as claimed in claim 10, and wherein the substantially cylindrically shaped lumen includes a longitudinally disposed groove, and wherein a tongue is made integral with the main body of the buccal tube insert and is operable to be slidably received in interlocking relation relative to the groove thereby impeding rotation of the buccal tube insert relative to the double buccal tube.

15. A buccal tube insert as claimed in claim 14 and wherein a deformable member is mounted on the second end of the main body and extends substantially longitudinally outwardly relative thereto, the deformable member being deformed substantially radially outwardly following placement of the buccal tube insert in the substantially cylindrically shaped lumen of the double buccal tube thereby impeding removal of the buccal tube insert from the substantially cylindrically shaped lumen.

16. A buccal tube insert as claimed in claim 15, and wherein the passageway has a square or rectangular cross-section which is substantially uniform along its entire length.

17. A buccal tube insert as claimed in claim 15, and wherein the passageway defined by the main body is a substantially longitudinally disposed slot which extends from the first end to the second end.

18. A buccal tube insert which is received within a cylindrically shaped lumen which is defined by a double buccal tube, the buccal tube insert comprising a substantially frusto-conically shaped main body having interior, and exterior facing surfaces, and opposite first and second ends, and wherein a circumscribing collar is made integral with the exterior facing surface and is located at the first end of the main body, and wherein the main body has a diametral dimension, when measured at the first end, which is greater than the diametral dimension of the lumen which is defined by the buccal tube, and wherein the interior facing surface defines a passageway which extends from the first to the second end, and wherein the exterior facing surface of the main body frictionally engages the buccal tube thereby releasably positioning the buccal tube insert in substantially fixed relation relative to the double buccal tube.

* * * * *